United States Patent
Estus et al.

(10) Patent No.: US 9,066,928 B1
(45) Date of Patent: Jun. 30, 2015

(54) METHOD, COMPOSITION, AND KIT USEFUL FOR TREATMENT OF ALZHEIMER'S DISEASE

(71) Applicant: UNIVERSITY OF KENTUCKY RESEARCH FOUNDATION, Lexington, KY (US)

(72) Inventors: Steven Estus, Lexington, KY (US); Manasi Malik, Lexington, KY (US); James Simpson, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 14/096,414

(22) Filed: Dec. 4, 2013

Related U.S. Application Data

(60) Provisional application No. 61/733,126, filed on Dec. 4, 2012.

(51) Int. Cl.
| | | |
|---|---|---|
| *A61K 38/00* | (2006.01) | |
| *A01N 37/18* | (2006.01) | |
| *A61K 39/395* | (2006.01) | |
| *A61K 45/06* | (2006.01) | |

(52) U.S. Cl.
CPC ............ *A61K 39/3955* (2013.01); *A61K 45/06* (2013.01)

(58) Field of Classification Search
None
See application file for complete search history.

(56) References Cited

U.S. PATENT DOCUMENTS

2014/0004081 A1* 1/2014 Cobbold et al. ............. 424/85.2

OTHER PUBLICATIONS

Carrasquillo et al., Mol. Neurodegeneration, 2011, 6(1):54.*
Yu-Lei Deng et al., Hum. Genetics, 2012, 131:1245-9.*
Hollingworth et al., Nature genetics, 2011, 43(5):429-35.*
Malik et al., J. Neurosci., 2013, 33(33):13320-5.*
Salminen et al., J. Mol. Med, 2009, 87:697-701.*
Vickers, Drug Ageing, 2002, 19(7):487-94.*
Naj, A.C., et al., Common variants at MS4A4/MS4A6E, CD2AP, CD33 and EPHA1 are associated with late-onset Alzheimer's disease. Nature genetics, 2011. 43(5): p. 436-41.
Lambert, J.C., et al., Meta-analysis of 74,046 individuals identifies 11 new susceptibility loci for Alzheimer's disease. Nat Genet, 2013. 45(12): p. 1452-8.
Bradshaw, E.M., et al., CD33 Alzheimer's disease locus: altered monocyte function and amyloid biology. Nat Neurosci, 2013. 16(7): p. 848-50.
Griciuc, A., et al., Alzheimer's disease risk gene CD33 inhibits microglial uptake of amyloid beta. Neuron, 2013. 78(4): p. 631-43.
Karch, C.M., et al., Expression of novel Alzheimer's disease risk genes in control and Alzheimer's disease brains. PLoS One, 2012. 7(11): p. e50976.

* cited by examiner

*Primary Examiner* — Olga N Chernyshev
(74) *Attorney, Agent, or Firm* — Stites & Harbison PLLC; Mandy Wilson Decker

(57) ABSTRACT

The presently-disclosed subject matter includes methods for treating Alzheimer's disease in a subject. The subject can have Alzheimer's diseases, can be identified has being at risk for developing Alzheimer's disease, or both. The method can comprise administering a composition that includes a CD33 inhibitor, which may include a CD33 antibody. In some embodiments the composition can further comprise at least one additional component useful for treating Alzheimer's disease. The presently-disclosed subject matter also includes compositions and kits for treating Alzheimer's disease in a subject.

6 Claims, 9 Drawing Sheets

SEQUENCE LISTING

```
<160> NUMBER OF SEQ ID NOS: 18

<210> SEQ ID NO 1
<211> LENGTH: 18
<212> TYPE: DNA
<213> ORGANISM: Artificial Sequence
```

```
<220> FEATURE:
<223> OTHER INFORMATION: Primer

<400> SEQUENCE: 1
ctcagacatg ccgctgct                                                    18

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ttcaatggcc atcatctcct                                                  20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
catcccatga aagttgaggg                                                  20

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
tactgctgcc cctgctgt                                                    18

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
tggccatcat ctcctgatct                                                  20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
aatgcagctc ctcatccatc                                                  20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
tgttccacag aacccaacaa                                                  20
```

```
<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ggctgtaaca ccagctcctc                                          20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ccctgctgtg ggcagacttg                                          20

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
gcaccgagga gtgagtagtc c                                        21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ctgtgcccga gctgtcttat                                          20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
aggctccttc ctacctgagc                                          20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gctgccacct tcactttacc                                          20

<210> SEQ ID NO 14
<211> LENGTH: 20
<212> TYPE: DNA
<213> ORGANISM: Artificial Sequence
<220> FEATURE:
<223> OTHER INFORMATION: Primer
```

```
<400> SEQUENCE: 14
ttgttgggtt ctgtggaaca                                                    20

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
cagctcaacg tcacctatgt tc                                                 22

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
cgtagaatcg agaccgagga                                                    20

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
tgcttactgg cttatcgaaa tta                                                23

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
tgtgggtcaa gtctgccc                                                      18
```

METHOD, COMPOSITION, AND KIT USEFUL FOR TREATMENT OF ALZHEIMER'S DISEASE

RELATED APPLICATIONS

This application claims priority from U.S. Provisional Patent Application No. 61/733,126, filed Dec. 4, 2012, the entire disclosure of which is incorporated herein by this reference.

GOVERNMENT SUPPORT

This invention was made with government support under Grant Nos. P01-AG030128, P30-AG028383, and P20-GM103436 awarded by the National Institutes of Health. The government has certain rights in the invention.

TECHNICAL FIELD

The presently-disclosed subject matter relates to the treatment of a subject having or identified as being at risk for developing Alzheimer's disease. In particular, the presently-disclosed subject matter relates to methods and compositions for treating Alzheimer's disease by reducing functional CD33 in a subject.

INTRODUCTION

Recent genome-wide association studies (GWASs) have identified a set of single nucleotide polymorphisms (SNPs) that are associated with Alzheimer's disease (AD) risk. One of the AD-associated SNPs, rs3865444, is in the proximal promoter of CD33. CD33 is a member of the sialic acid-binding Ig-like lectin (SIGLEC) family of receptors However, there has been limited progress in elucidating the mechanisms of action underlying such SNPs. This difficulty can be attributed to variability in human gene expression due to diversity in genetics and environment, including diet and drug exposure. The difficulty can also be attributed to the fact that the brain contains heterogeneous cell types, and controlling for variation in the proportion of cell types between samples is challenging. Lastly, AD-associated SNPs from GWAS are not typically functional, but rather are in linkage disequilibrium (LD) with functional SNP(s), which introduces variability.

Elucidating the mechanism of action of these SNPs could potentially be beneficial for identifying novel Alzheimer's disease pathways. Indeed, genetic variation that modulates disease risk could be considered to biologically define rate-limiting steps in Alzheimer's disease pathways, and, as such, lead to robust new pharmacologic targets. For example, an SNP with modest biological actions may reduce Alzheimer's disease risk modestly, whereas a drug that acts strongly at the same target may have a large effect on Alzheimer's disease risk reduction. Elucidating the mechanism of action of AD-associated SNP may therefore lead to the development of treatments for Alzheimer's disease.

Hence, there remains a need to elucidate the mechanism of action of AD-associated SNPs. There also remains a need to develop novel compositions and methods for treating Alzheimer's disease that are based on information elucidated form particular AD-associated SNPs.

DESCRIPTION OF EXEMPLARY EMBODIMENTS

Figure 1A:
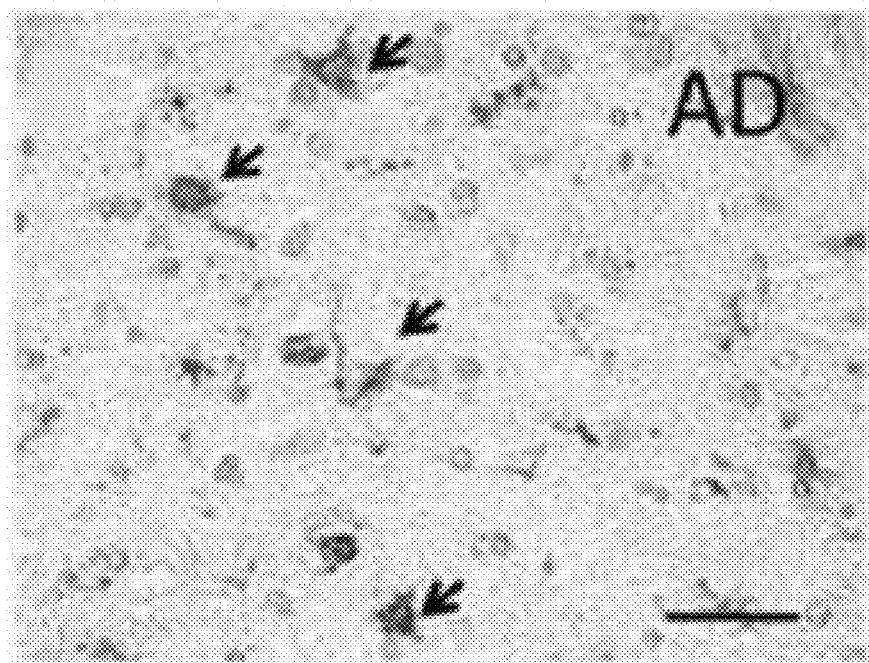
FIG. 1 includes CD33 immunohistochemistry images in human brain showing CD33-immunopositive cell profiles (arrows) that have a morphology consistent with microglia in both Alzheimer's disease (AD) and non-AD samples (A, B); and also includes immunofluorescence images used to help distinguish CD33-immunopositive cell types, where (C-H) show the same microscope fields and show sections immunostained for CD33 and counterstained for IBA-1 (a microglial/macrophage lineage marker) or GFAP (an astrocyte lineage marker). Sections were from superior/middle temporal gyri of subjects with AD pathology (A, C-H) or without (B) AD pathology. Ctrl, Control. Scale bar: a, b, 50 µm; c-h, 20 µm.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polynucleotides and polypeptides identified herein include sequence and other information in the GEN-BANK®/GENPEPT® database, which sequence and other information is expressly incorporated by reference. Unless otherwise indicated or apparent, the references to the GEN-BANK®/GENPEPT® database are references to the most recent version of the database as of the filing date of this Application.

The presently-disclosed subject matter includes methods, compositions, and kits useful for the treatment of Alzheimer's disease (AD) in a subject. In some embodiment, the subject has Alzheimer's disease. In some embodiments, the subject is identified as being at risk for developing Alzheimer's disease. As such, treatment of Alzheimer's disease is not limited to treatment of subjects who have already been diagnosed with Alzheimer's disease, but is inclusive of the treatment of subjects who are identified as having an increased risk of Alzheimer's disease as compared to the general population. The phrase "increased risk" is used herein to refer to those subjects whose likelihood of developing a Alzheimer's disease in their lifetime is increased, as compared to a normal subject. Furthermore, the subject can be a human subject or a non-human subject.

In some embodiments, the subject is identified has having a single nucleotide polymorphism associated with risk of developing Alzheimer's disease. In this regard, certain mechanisms identified by these SNPs constitute "bottlenecks" in Alzheimer's disease pathways. These bottlenecks can biologically define rate-limiting steps in Alzheimer's disease pathways, and, as such, can constitute targets for treatment. For example, a SNP may reduce Alzheimer's disease risk modestly (e.g., 10%), but a drug that acts strongly at the same target may have a more robust (e.g., 10-50%) effect on Alzheimer's disease risk and gene function.

In some embodiments, the SNP is the CD33 polymorphism, rs3865444. rs3865444 (rs444), a SNP near CD33, appears to be AD-associated, as shown in cohorts totaling more than 48,000 individuals (odds ratio=0.89, $p=10^{-9}$). The present inventors identified the effect of rs444 on CD33 as well as different CD33 isoforms expressed in human brain. In certain subjects, a CD33 isoform containing all seven CD33 exons can be relatively common, as can be nonfunctional CD33 isoforms, such as those lacking exon 2 (D2-CD33) or those retaining intron 1 (Int1-CD33).

Figure 3:
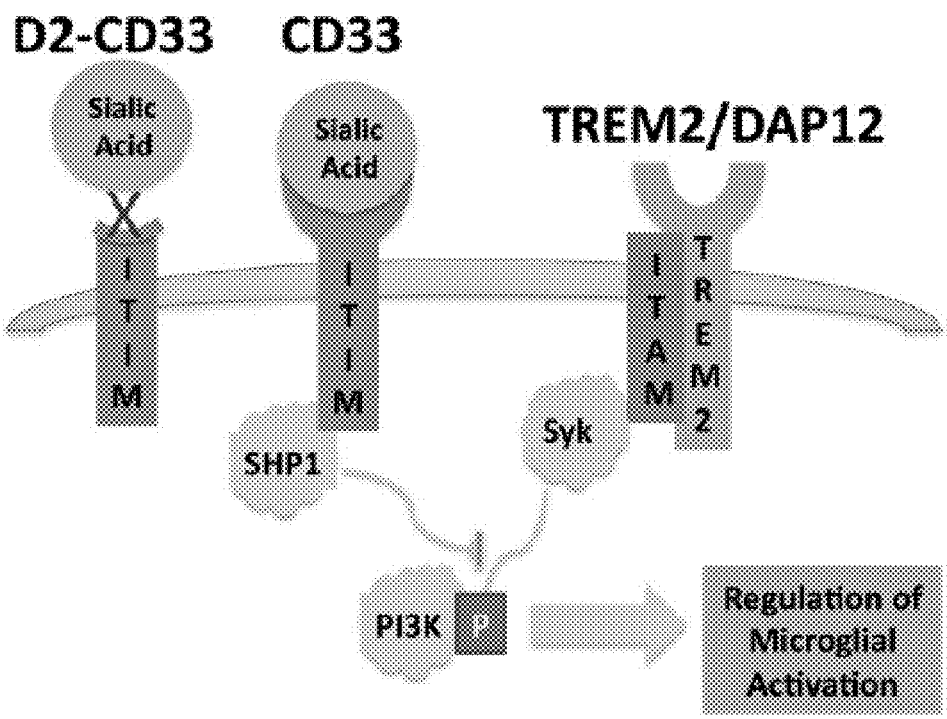
FIG. 3 includes a schematic showing the mechanisms for CD33 and TREM2 in microglial activation, where sialic acid binding to CD33 results in activation of SHP1 phosphatase that inhibits immune cell activation, the D2-CD33 isoform lacks the exon that encodes the apparent sialic acid binding domain, and a ligand binds TREM2 that signals through DAP12 to activate the tyrosine kinase Syk, resulting in microglial activation.

Thus, the present-disclosed subject matter provides an understanding of how Alzheimer's disease risk can be modulated by genetic factors that influence microglial activation. Increased Alzheimer's disease risk has been associated with apparent inactivating mutations in the microglial activator TREM2, and TREM2 acts via DAP12 to activate Syk mediated tyrosine phosphorylation to promote microglial phagocytosis (FIG. 3). The present inventors found that rs3865444A is associated with lower overall CD33 expression as well as exclusion of CD33 exon 2 and possibly other nonfunctional CD33 (e.g., Int1-CD33).

In this regard, sialic acids activate CD33 to stimulate SHP1/SHP2 tyrosine phosphatases, resulting in inhibition of phagocytosis (FIG. 3). Because D2-CD33 lacks the IgV domain that is predicted to mediate sialic acid binding, D2-CD33 likely encodes a nonfunctional protein. Consistent with this, phagocytosis as measured by $A\beta_{42}$ uptake has been found to be inhibited when BV2 cells are transfected with CD33, but not CD33 lacking the IgV domain. Hence, D2-CD33 likely represents a loss of CD33 function. Therefore, it appears that TREM2 and CD33 act in opposing directions to modulate tyrosine phosphorylation and, thereby, microglial activation and AD risk. Alleles that inhibit TREM2 function may increase Alzheimer's disease risk, whereas alleles that inhibit CD33 function may reduce Alzheimer's disease risk.

Thus, the presently-disclosed subject matter relates to protective SNP alleles as well as Alzheimer's disease treatment methods and compositions that are based on the same. In certain subjects the AD-protective rs444A allele is associated with an about 10% per allele increase in the expression of CD33 lacking exon 2 (D2-CD33). Certain embodiments of the presently-disclosed subject matter relate to methods and compositions for treating Alzheimer's disease by reducing functional CD33 and/or by reducing a ratio of functional CD33 to nonfunctional CD33.

As used herein, the terms "treatment" or "treating" are inclusive of prophylactic treatment and therapeutic treatment. As such, the terms treatment and treating include: preventing the disease from occurring in a subject who may be predisposed to the disease but who has not yet been diagnosed as having it; inhibiting the disease, including arresting the progression or development of the disease; reducing the severity of the disease; ameliorating or relieving the symptoms of the disease; causing regression of disease; curing the disease; and/or stabilizing the disease. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes preventative treatment, that is, treatment directed to minimizing or partially or completely inhibiting the development of the associated disease, pathological condition, or disorder.

In some embodiments, the method includes administering a composition for reducing functional CD33 in the subject, wherein the subject has Alzheimer's disease or is identified as being at risk for developing Alzheimer's disease. In some embodiments, the method includes administering a composition for reducing functional CD33 in the subject, wherein the subject is identified as having a single nucleotide polymorphism associated with risk of Alzheimer's disease, e.g., rs3865444, rs12459419, or combinations thereof.

The term "administering" refers to any method of providing a composition and/or pharmaceutical composition thereof to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, subcutaneous administration, intravitreous administration, intracameral (into anterior chamber) administration, subretinal administration, sub-Tenon's administration, peribulbar administration, administration via topical eye drops, and the like. Administration can be continuous or intermittent. In various aspects, a preparation can be administered therapeutically; that is, administered to treat an existing disease or condition (e.g., exposure to OP compounds). In further various aspects, a preparation can be administered prophylactically; that is, administered for prevention of a disease or condition.

In some embodiments, the composition administered can include a CD33 inhibitor. The CD33 inhibitor can be selected, for example, from a polypeptide inhibitor (including oligonucleotide inhibitor), a small molecule inhibitor, an siRNA inhibitor, an antibody, an aptamer, a dominant negative plasmid or vector inhibitor, and combinations thereof.

In this regard, the term "inhibit" or the like does not necessarily refer to the ability to completely inactivate all target biological activity in all cases. Rather, the skilled artisan will understand that the term "inhibit" refers to a decrease biological activity of a target, such as a decreasing expression of CD33 and/or functional CD33. This can occur by various mechanisms, including, but not limited to, altering the structure of a protein so that its intended function is limited or eliminated in in a biochemical pathway, blocking particular binding sites in a biological pathway, or the like. Such decrease in biological activity (i.e., inhibition) can be determined relative to a control, wherein an inhibitor is not administered and/or placed in contact with the target. For example, in some embodiments, a decrease in activity relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease. The term "inhibitor" refers to a compound of composition that inactivates or decreases the biological activity, such as CD33 inhibitors that inactivate or decrease the biological activity of CD33.

In specific embodiments the composition administered can include a CD33 inhibitor that includes an antibody, wherein the antibody is a CD33 antibody. A non-limiting example of a CD33 antibody that could be used in connection with the presently-disclosed subject matter is lintuzumab. Another exemplary CD33 antibody can include P67.6. In some embodiments the CD33 inhibitor can include two or more different antibodies, some or all of which can be CD33 antibodies. In some embodiments wherein the subject is administered a CD33 inhibitor, such as a CD33 antibody, the subject is not being treated for a cancer.

Despite the various approaches, in some embodiments the administered composition includes humanized monoclonal antibodies against CD33, which have been developed for treatment of acute myeloid leukemia (AML). Antibodies (e.g., monoclonal antibodies targeting CD33) that can be used in conjunction with the present compositions, methods, and kits include "naked" antibodies, such as Lintuzumab, which is merely an antibody. Alternatively or additionally, the provided antibodies in certain embodiments can be conjugated to another biologically active agent, such as the conjugated compound Gemtuzumab ozogamicin. Antibodies such as "Lintuzumab" show specificity and target engagement in the periphery as well as a safety profile marked by minimal side effects. As CD33 antagonists, CD33 antibodies including Lintuzumab down-regulate CD33 from the cell surface in vivo and in vitro. Hence, antibodies such as Lintuzumab represent immunoreagents with specificity and peripheral efficacy in target engagement, an acceptable safety profile, and demonstrated ability to antagonize CD33.

In some embodiments, the method includes administering a CD33 inhibitor, which can itself include a CD33 antibody, and further includes administering a composition including at least one component useful for treating Alzheimer's disease. In some embodiments, the method includes administering a composition including a CD33 inhibitor and/or a CD33 antibody, and further including another component useful for treating Alzheimer's disease. Examples of such components include, but are not limited to, Razadyne® (galantamine), Exelon® (rivastigmine), Aricept® (donepezil), Cognex® (tacrine), and Namenda® (memantine). Exemplary components use for treating Alzheimer's disease also can include vitamin E.

Further still, other exemplary components for treating (e.g., ameliorating the symptoms of) Alzheimer's disease, and which can be administer in conjunction with a CD33 inhibitor, include antidepressants, such as Celexa® (citalopram), Prozac® (fluoxetine), Paxil® (paroxetine), and Zoloft® (sertraline), anxiolytics, such as Ativan® (lorazepam) and Serax® (oxazepam), antipsychotic medications, such as Abilify® (aripiprazole), Haldol® (haloperidol), Zyprexa® (olanzapine), clozapine, risperidone, quetiapine, and ziprasidone, anti-anxiety medications, such as benzodiazepines (e.g., Valium® (diazepam) or Ativan® (lorazepam)) and non-benzodiazepines (e.g., Buspar® (buspirone)).

In some embodiments, a method for treating Alzheimer's disease in a subject is provided that comprises administering a composition for reducing functional CD33, and further comprises administering another treatment for Alzheimer's disease. The subject can have and/or be identified as being at risk for developing Alzheimer's disease. The other treatment can include any of the compositions described herein. Exemplary treatments for Alzheimer's disease can also include hormone replacement therapy, sensory therapies, other therapies, such as coenzyme Q10, coral calcium, huperzine A, and omega-3 fatty acids.

In some embodiments of the present methods, the administered composition increases a ratio of nonfunctional CD33 to functional CD33 in the subject. In some embodiments the compositions sustain approximately the same level of functional CD33 and activate (i.e., increases the level of) nonfunctional CD33. In some embodiments the compositions reduce a level of functional CD33 and sustain approximately the same level of nonfunctional CD33. Further still, in some embodiments the compositions both reduce a level of (i.e., inhibit) functional CD33 and activate nonfunctional CD33.

Nonfunctional CD33 refers to any CD33 that includes a mutation that alters, inhibits, or otherwise compromises the normal biological activity of CD33. This includes CD33 having one or more deleterious SNPs. Nonfunctional CD33 also includes some fragments of functional CD33. Exemplary nonfunctional CD33 includes CD33 lacking exon 2 (D2-CD33), CD33 retaining intron 1 (Int1-CD33), and the like. Accordingly, in some embodiments of the present methods the compositions can increase a ratio of nonfunctional CD33, which can include D2-CD33, Int1-CD33, or combinations thereof, to functional CD33 in the subject.

In some embodiments the subject that is being treated for Alzheimer's disease is not being further treated for cancer. Therefore, in some embodiments, the subject has not been diagnosed as having cancer and/or has not been identified as having a risk for developing cancer. In specific embodiments the subject does not have, has not been diagnosed as having, and/or has not been identified as being at risk for developing acute myeloid leukemia (AML). In this regard, in some embodiments the present methods are performed only for the purpose of treating Alzheimer's disease.

The presently-disclosed subject matter further includes a composition comprising a CD33 inhibitor and at least one additional component useful for treating Alzheimer's disease. As described herein, the CD33 inhibitor can include a polypeptide inhibitor, a small molecule inhibitor, an siRNA inhibitor, an antibody, an aptamer, a dominant negative plasmid or vector inhibitor, and combinations thereof. Furthermore, the CD33 inhibitor can include a CD33 antibody, such as lintuzumab, P67.7, or combinations thereof. Also as discussed herein, the at least one additional component useful for treating Alzheimer's disease can include, but is not limited to, galantamine, rivastigmine, donepezil, tacrine, memantine, vitamin E, and combinations thereof.

Embodiments of the present compositions are capable of increasing a ratio of nonfunctional CD33 to functional CD33 in a subject. Alternatively or additionally, exemplary compositions can also be capable of activating nonfunctional CD33 in a subject, such as, but not limited to, D2-CD33 and/or Int1-CD33.

Additionally, the presently-disclosed subject matter includes pharmaceutical compositions. Exemplary pharmaceutical compositions can comprise any of the compositions described herein as well as a pharmaceutically acceptable carrier.

The term "pharmaceutically acceptable carrier" refers to sterile aqueous or nonaqueous solutions, dispersions, suspensions, emulsions, or nanoparticle delivery systems, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The presently-disclosed subject matter further includes a kit comprising a CD33 inhibitor, and at least one additional component useful for treating Alzheimer's disease. In some embodiments the kit comprises a CD33 inhibitor that includes an antibody, and at least one additional component useful for treating Alzheimer's disease.

In some embodiments, kits can further include a device for administering the CD33 inhibitor and/or a device for administering the at least one additional component. The kit can comprise one device for administering the CD33 inhibitor and the additional component, or may comprise one device for each of the CD33 inhibitor and the additional component. The ordinary artisan will appreciate certain devices that can be utilized in conjunction with the present kits. For instance, injectable CD33 inhibitors, additional components, or both can be administered by a device that includes, but is not limited to, a syringe, a hypodermic needle, a catheter, or the like.

Further still, the presently-disclosed subject matter relates to novel methods for elucidating the mechanism of particular SNPs. In some embodiments the methods comprise analyzing quantitative gene expression as a function of splice variants and/or of cell-type variation among biological samples, such as brain samples. By looking at quantitative gene expression in this relative manner, previous difficulties associated with characterizing the function of particular SNPs can be avoided or minimized.

Such difficulties included the inability to evaluate the effects of particular gene expression due to the inherent variability in gene expression due to genetic and environmental conditions. Difficulties also included the inability to control the relatively types and concentrations of cells between different biological samples, which can include heterogeneous cell types. Thus, the present methods of analyzing quantitative gene expression as a function of splice variants and/or analyzing quantitative gene expression as a function of cell-type variation among biological samples, can avoid certain inherent and possibly ambiguous variations that were present in previous methods.

In particular embodiments, as described herein, the present methods include a combination of qPCR assays specific to individual CD33 isoforms, controlling for microglial content in samples, and/or recognizing that the functional polymorphism is linked with the Alzheimer's disease SNP (rs444). This method allowed the present inventors to elucidate the mechanism associated with various SNPs, including rs444. This method can be extended to elucidate the mechanism associated with other SNPs that are associated with Alzheimer's disease. The present methods can also be extended to elucidate the mechanism associated with SNPs that are not associated with Alzheimer's disease.

The presently-disclosed subject matter is further illustrated by the following specific but non-limiting examples. Some of the following examples are prophetic, notwithstanding the numerical values, results and/or data referred to and contained in the examples. Additionally, the following examples may include compilations of data that are representative of data gathered at various times during the course of development and experimentation related to the present invention.

EXAMPLES

Example 1

This Example describes procedures used to elucidate the mechanisms of the AD risk allele, rs3865444, and CD33. In particular, this Example demonstrates that CD33 expression is primarily microglial, that CD33 expression is increased in AD, and that the AD-protective rs3865444A allele acts via its proxy, rs12459419T, to increase the proportion of CD33 (functional CD33) expressed as nonfunctional CD33 (e.g., D2-CD33). This Example thus identifies a novel mechanism for the protective allele of CD33 as well as potential treatments that include CD33 modulation in subjects having and/or at risk for developing AD.

De-identified human brain specimens were provided by the University of Kentucky Alzheimer's Disease (AD) Center Neuropathology Core (Lexington, Ky.). Samples were from 30 women (14 non-AD and 16 AD) and 25 men (13 non-AD and 12 AD). AD and non-AD designations were by consensus conference, with disease being defined based on dementia and AD neuropathology, i.e., neuritic plaques and neurofibrillary tangles. RNA and DNA were prepared from these samples.

To perform CD33 immunostaining paraffin-embedded tissue sections were cut at 5 µm, followed by antigen retrieval in citrate buffer, pH 6.0, using a pressure cooker (3 min). Sections were immersed in 5% goat serum in Tris-buffered saline, followed by an overnight incubation in anti-CD33 (clone PWS44; 1:100 dilution; Leica). After thorough rinsing in Tris-buffered saline, sections were incubated in biotinylated secondary antibody for 1 h, rinsed, incubated in ABC reagent (Vector Laboratories, Burlingame, Calif.) for 1 h, developed in Nova Red chromagen (Vector Laboratories), and counterstained with Mayer's hematoxylin. For immunofluorescence, sections were treated similarly. Sections were then labeled with CD33 antibody (1:100), IBA-1 (rabbit polyclonal, 1:1000; Wako Chemicals, Richmond, Va.), and/or GFAP (rabbit polyclonal, 1:10,000; Dako, Carpinteria, Calif.), rinsed, and detected with labeled secondary antibodies (antirabbit DyLight 488-labeled anti-rabbit, 1:500; Jackson Laboratories, Bar Harbor, Me.; or Texas Red labeled anti-mouse, 1:500; Jackson Laboratories). Autofluorescence eliminator reagent (Millipore Bioscience Research Reagents, Billerica, Mass.) was used to block autofluorescence.

To identify CD33 splice variants in human brain, screening for CD33 splice variants was performed on a pool of four cDNA samples representing AD and non-AD individuals and varying rs3865444 genotypes. Nested PCR was used to amplify CD33 exons 1-7A and exons 1-7B in separate reactions. An initial 20 cycles of PCR (Platinum Taq; Invitrogen, Carlsbad, Calif.) was performed by using forward primer 5'-CTCAGACATGCCGC TGCT-3' (SEQ ID NO: 1) corresponding to exon 1 and reverse primers 5'-TTCAATGCC-CATCATCTCCT-3' (SEQ ID NO: 2) and 5'-CATCCCAT-GAAAGTTGAGGG-3' (SEQ ID NO: 3), corresponding to exons 7A and 7B, respectively. The PCR product was then diluted 1:25 and subjected to 30 cycles of amplification using forward primer 5'-TACTGCTGCCCCTGCTGT-3' (SEQ ID NO: 4) from exon 1 and 5'-TGGCCATCATCTCCTGATCT-3' (SEQ ID NO: 5) and 5'-AATGCAGCTCCTCATCCATC-3' (SEQ ID NO: 6) corresponding to exons 7A and 7B, respectively. PCR consisted of an initial 3-min 94° incubation, followed by cycles of denaturation at 94° for 15 s, annealing at 60° for 15 s, and extension at 72° for 2 min (Veriti 96-Well Thermal Cycler; Invitrogen). PCR was conducted using 1 µM the indicated primers (1 µM) and ~0.1 µg of cDNA template. After PCR, samples were incubated at 72° for 30 min and then cloned into pcDNA2.1 according to the instructions of the manufacturer (TA-Cloning Kit; Invitrogen). Twenty-five random clones were picked from each group amplification reaction (exons 1-7A, exons 1-7B) and sequenced by using M13 forward and reverse primers. In addition to common D2-CD33, one to two clones had both exons 7A and 7B, skipped other exons, or retained intron 1 (Int1-CD33).

Quantitative PCR (qPCR) was used to quantify expression of total CD33 (forward, 5'-TGTTCCACAGAACCCAA-CAA-3'(SEQ ID NO: 7); reverse, 5'-GGCTGTAACAC-CAGCTCCTC-3' (SEQ ID NO: 8)) primers corresponding to sequences within exons 4 and 5, respectively. qPCT was also used to quantify expression of total D2-CD33 (forward, 5'-CCCTGCTGTGGGCAGACTTG-3' (SEQ ID NO: 9); reverse, 5'-GCACCGAGGAGTGAGTAGTCC-3'(SEQ ID NO: 10)) primers corresponding to sequences at the exon 1-3 junction and exon 3, respectively. The specificity of the 1 to 3 junctional primer was confirmed by testing on CD33 sequence fragments containing or lacking exon 2, as well as post-qPCR melting curve analysis and gel electrophoresis of PCR products. PCR was conducted using an initial 2 min incubation at 95°, followed by cycles of 10 s at 95°, 20 s at 60°, and 20 s at 72°. The 20 µl reactions contained 1 µM each primer, 1X PerfeCTa SYBR Green Super Mix (Quanta Biosciences, Gaithersburg, Md.), and 20 ng of cDNA. Experimental samples were amplified in parallel with serially diluted standards that were generated by PCR of cDNA using the indicated primers, followed by purification and quantitation by UV absorbance. Results from samples were compared relative to the standard curve to calculate copy number in each sample. Real-time assays were performed twice, and the average copy number was used for additional data analyses.

To evaluate the correlation between CD33 and that of microglial mRNAs, CD11b and AIF-1 expression was also quantified. The copy number for each mRNA was then normalized to the geometric mean of reference genes RPL32 and EIF4H, previously quantified in this sample set. Because CD33 expression correlated with CD11b and AIF-1, total CD33 expression was compared to the geometric mean of CD11b and AIF-1 expression when analyzing CD33 expression relative to AD status and rs3865444 genotype, correcting for the microglial content of brain tissue samples from which the cDNA was originally prepared. Expression of D2-CD33 was analyzed relative to total CD33 expression. To screen for CD33 SNPs that may be tightly linked to rs3865444 and modulate exon 2 splicing, seven individuals homozygous for the major or minor allele of rs3865444 were sequenced from 400 bp 5' to the transcription start site through exon 4. Nested PCR was conducted according to the directions of the manufacturer (Phusion High-Fidelity DNA Polymerase; New England Biolabs, Ipswich, Mass.); 20 PCR cycles were conducted with forward primer 5'-CTGTGCCCGAGCTGTCT-TAT-3'(SEQ ID NO: 11) and reverse primer 5'-AGGCTCCT-TCCTACCTGAGC-3' (SEQ ID NO: 12). PCR products were then diluted 1:25 and used in a second round of PCR (25 cycles) using the forward primer 5'-GCTGCCACCT-TCACTTTACC-3' (SEQ ID NO: 13) with reverse primer 5'-TTGTTGGGTTCTGTGGAACA-3'(SEQ ID NO: 14).

The first round of PCR used about 80 ng of genomic DNA in a 20 µl reaction with both PCRs conducted using 3%

DMSO. This process identified four SNPs in this region: (1) rs3865444, the AD-associated promoter SNP; (2) rs2459141, which is 142 bp upstream of the transcription start site; (3) rs12459419 at the fourth base of exon 2; and (4) rs2455069 at the 168th base of exon 2. rs12459419 was linked with rs3865444 in these samples. Samples were subsequently genotyped for rs12459419 by using a TaqMan approach (Invitrogen); rs3865444 genotypes were determined by NcoI restriction fragment length polymorphism.

CD33 minigenes containing exon 1 through exon 4 and differential for rs12459419C/T were generated by PCR and cloned into pcDNA3.1 (Invitrogen). Sequencing confirmed that the inserts differed only at rs12459419C/T. BV2 microglial cells were maintained in DMEM/F-12 (Invitrogen) supplemented with a final concentration of 10% fetal bovine serum, 50 U/ml penicillin, and 50 µg/ml streptomycin. Cells were seeded in six-well plates ($2 \times 10^5$ cells per well) and allowed to grow for 24 h before transfection with 1 µg of allele-specific CD33 minigene vector in 6 µl of Lipofectamine 2000 reagent (Invitrogen) and 94 IA of Opti-MEM, per the recommendations of the manufacturer. Eighteen hours after transfection, poly(A+) RNA was prepared and reverse transcribed by using random hexamers per the directions of the manufacturer (SuperScript III; Invitrogen). Three transfections were performed in duplicate for each allele. CD33 and D2-CD33 expression from the minigene was quantified by qPCR using primers corresponding to exon 3-4 junction and 3' vector-derived sequence (5'CAGCTCAACGTCAC-CTATGTTC (SEQ ID NO: 15) and 5'CGTAGAATC-GAGACCGAGGA (SEQ ID NO: 16)) and 5' vector and the exon 1-3 junction (5'TGCTTACTGGCTTATCGAAATTA (SEQ ID NO: 17) and 5'TGTGGGTCAAGTCTGCCC (SEQ ID NO: 18)), respectively. A one-tailed t test was used to analyze the results.

Figure 1B:
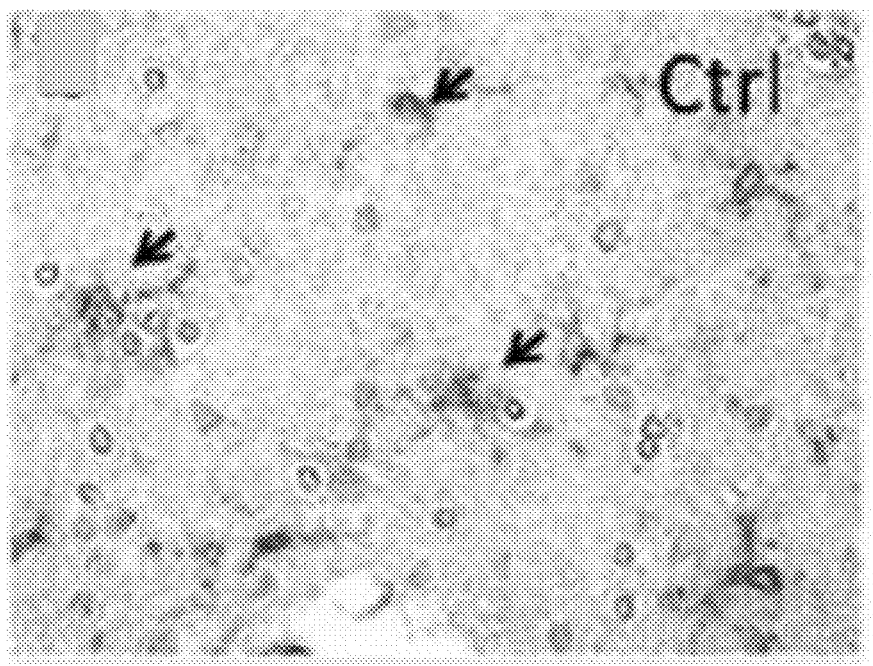
Figure 1C:
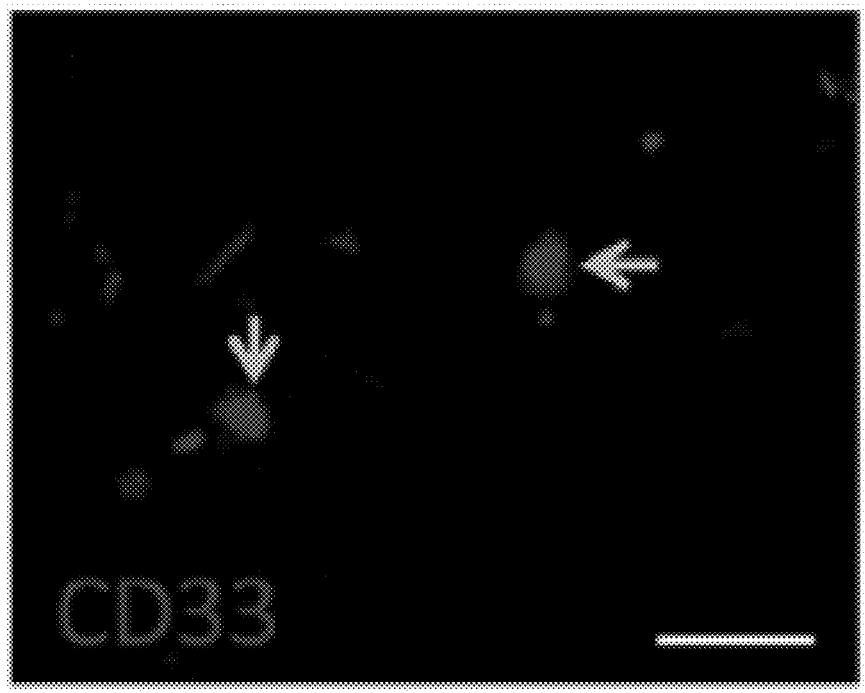
Figure 1D:
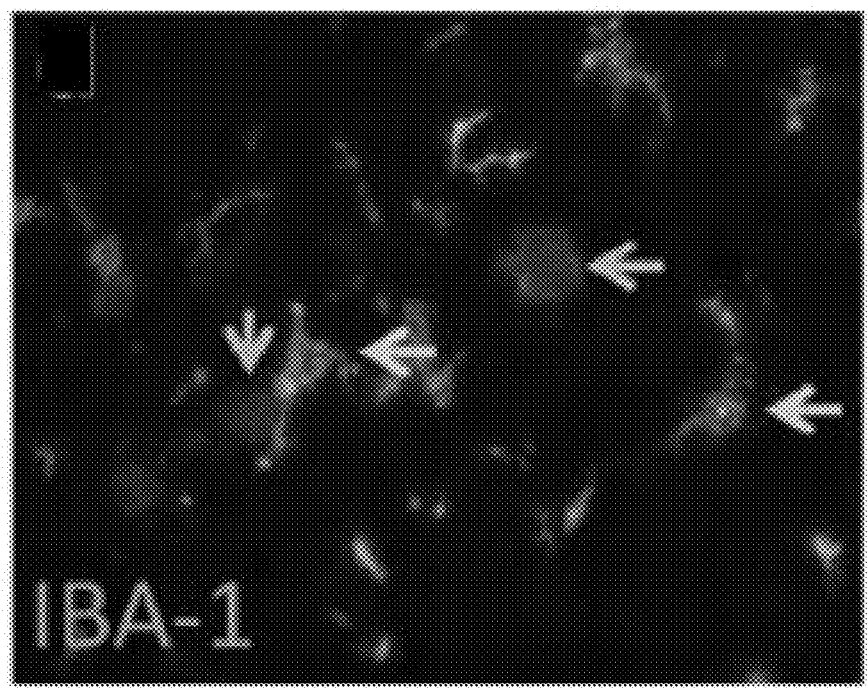
Figure 1E:
Figure 1F:
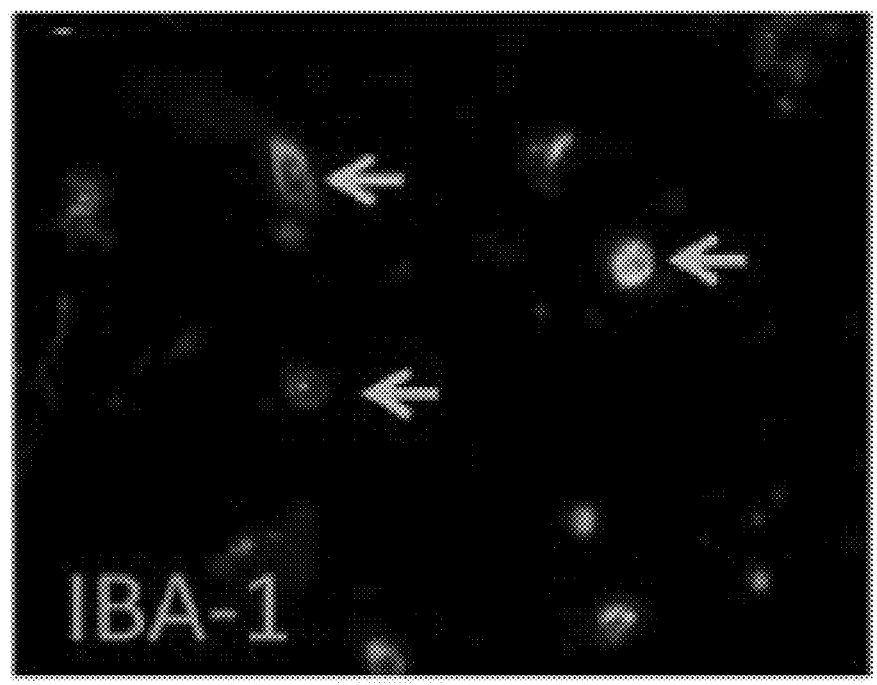
Figure 1G:
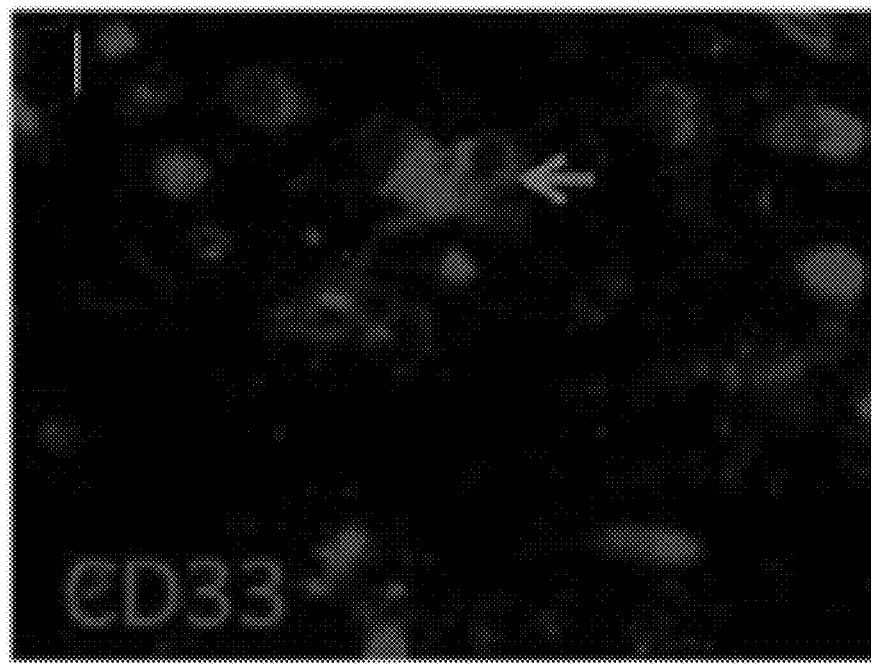
Figure 1H:
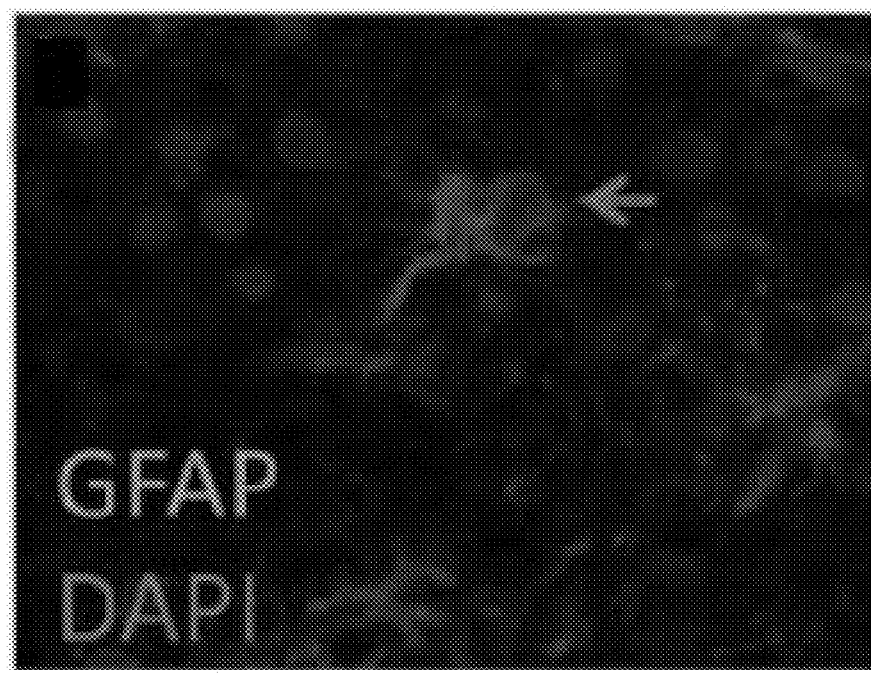

Immunocytochemistry that localized CD33 expression in human brain showed that CD33 expression in microglia, as discerned by morphology (FIGS. 1A and 1B). Microglial localization was confirmed by double labeling brain sections for CD33 and IBA-1, a microglial protein, or GFAP, an astrocytic protein (FIGS. 1C to 1F). Overall, predominant microglial localization is consistent with the potential role of CD33 as a sialic acid receptor that inhibits monocyte-lineage cell activation.

Figure 4:
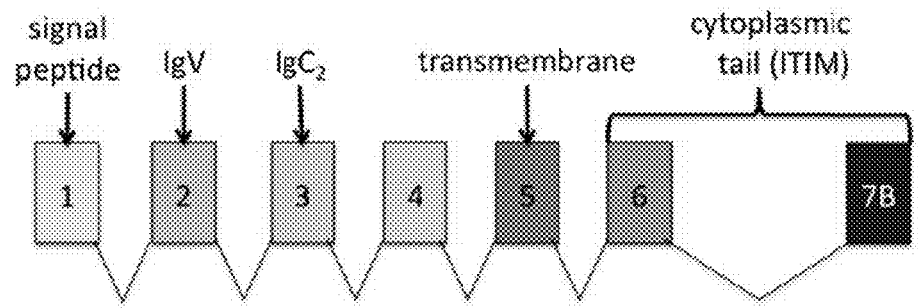
FIG. 4 includes a schematic showing the gene structure for CD33.
Figure 5A:
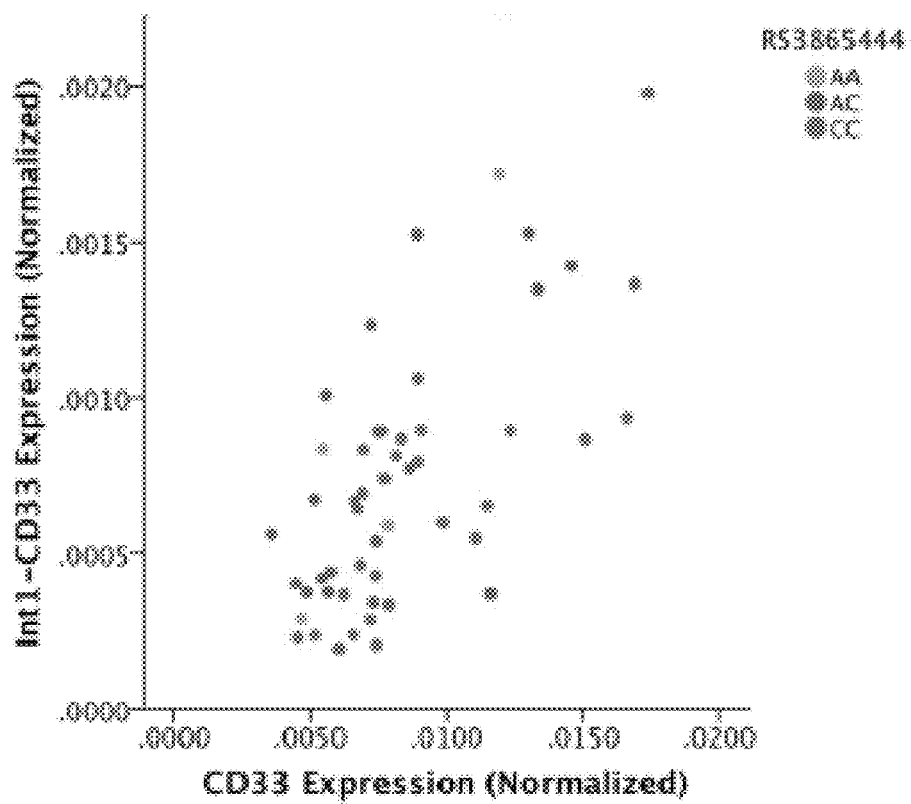
FIG. 5 includes charts of Int1-CD33 expression relative to Alzheimer's disease status, showing (A) Int1-CD33 expression correlated with CD33 expression, (B) the percentage of CD33 expressed as Int1-CD33 associated with the rs3865444 genotype, (C) total non-functional CD33 correlated with CD33 expression, and (D) the percentage of CD33 expressed as non-functional CD33 associated with the rs3865444 genotype.
Figure 5B:
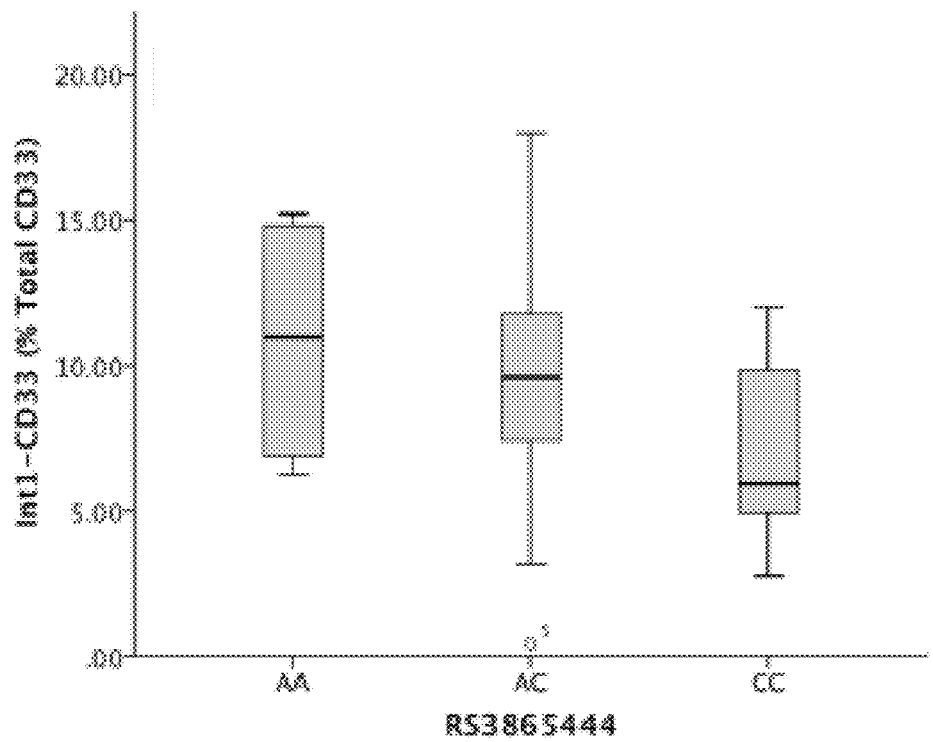
Figure 5C:
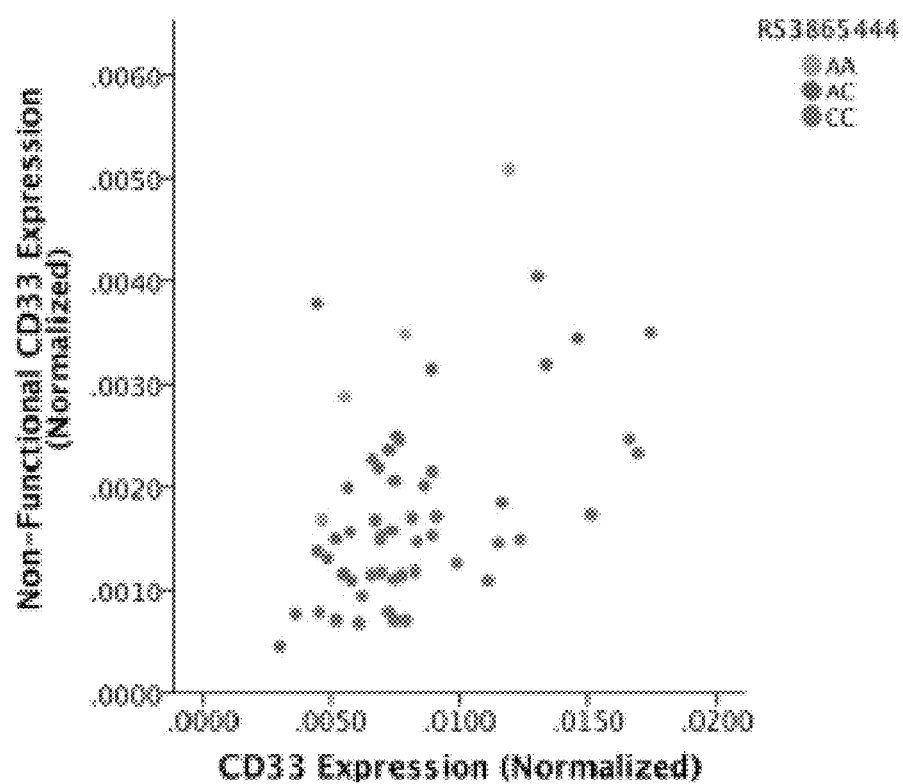
Figure 5D:
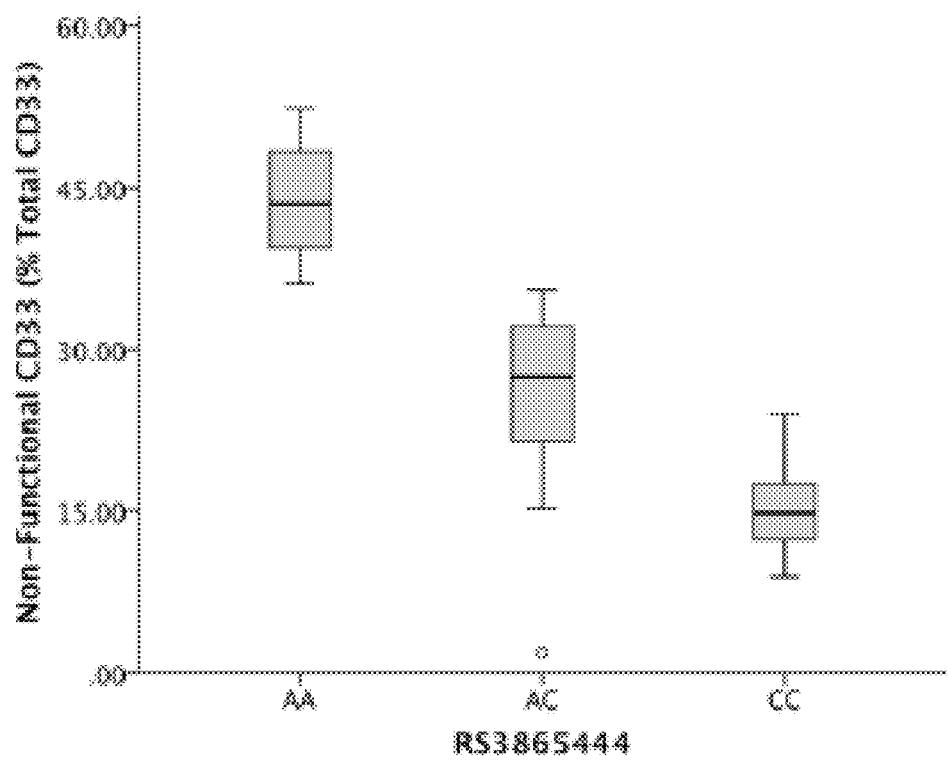

As discussed above, CD33 is encoded by seven exons, including the alternatively spliced exons 7A and 7B (see, e.g., FIG. 4). Common CD33 isoforms in human brain were found using PCR amplification on human brain cDNA using primers corresponding to exon 1 and exon 7A or 7B. Sequencing 50 random clones revealed frequent isoforms lacking the 381 bp exon 2 (D2-CD33). Because the codon reading frame is maintained in the absence of exon 2, D2-CD33 encodes a protein that is identical to CD33, but that lacks the IgV domain that mediates sialic acid binding in SIGLEC family members. Both D2-CD33 and CD33 were found on the cell surface of transfected cells.

Figure 2A:
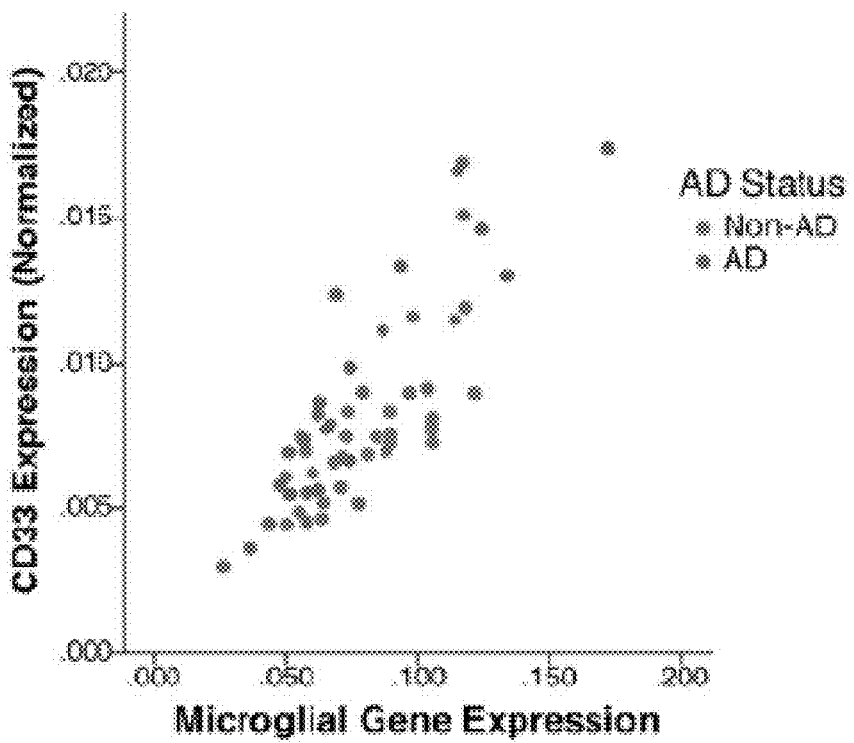
FIG. 2 includes charts of CD33 isoform expression relative to Alzheimer's disease status, showing (A) CD33 expression correlated with microglial gene expression (presented as geometric mean of CD11b and AIF-1, $r^2$=0.64), (B) association between CD33 and Alzheimer's disease status visualized by considering the ratio of CD33 to the geometric mean of the microglial reference genes, (C) D2-CD33 correlated with CD33 expression ($r^2$=0.88, 0.67, and 0.51 for the AA, CA, and CC genotypes, respectively), and (D) the percentage of CD33 expressed as D2-CD33 associated with the rs3865444 genotype (p=$1.2 \times 10^{-13}$).
Figure 2B:
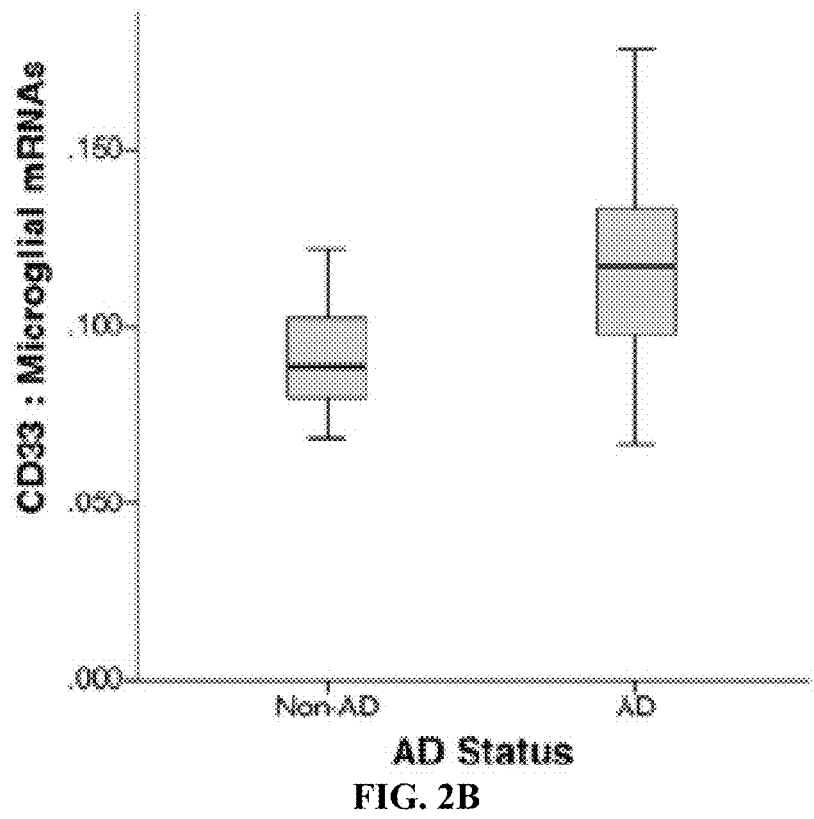

Without being bound by theory or mechanism, rs3865444 modulates CD33 expression since this SNP is 372 bp upstream of the CD33 transcription start site. To analyze this finding, CD33 expression was assessed by performing qPCR with primers corresponding to sequence within exons 4 and 5. As described above, since immunostaining suggested that CD33 localized primarily to microglia, CD33 expression was analyzed relative to the geometric mean of two microglial mRNAs, CD11b and AIF-1 (IBA-1), as well as AD status and rs3865444 genotype. It was observed that CD33 expression correlated strongly with microglial mRNA expression, was increased in AD, and was decreased with the AD-protective rs3865444A allele (FIGS. 2A and 2B). Similarly, regression analysis showed a highly significant model (adjusted $r^2=0.76$) wherein CD33 expression correlated significantly with microglial gene expression ($p=3.3\times10^{-16}$, standardized $\beta$ coefficient of 0.78), AD status ($p=5.9\times10^{-6}$, standardized 0 coefficient of 0.29), and rs3865444 genotype ($p=0.012$, standardized $\beta$ coefficient of $-0.17$). These results are consistent with CD33 expression in microglia, increased CD33 expression in AD, and decreased CD33 expression with the protective rs3865444A allele.

Figure 2C:
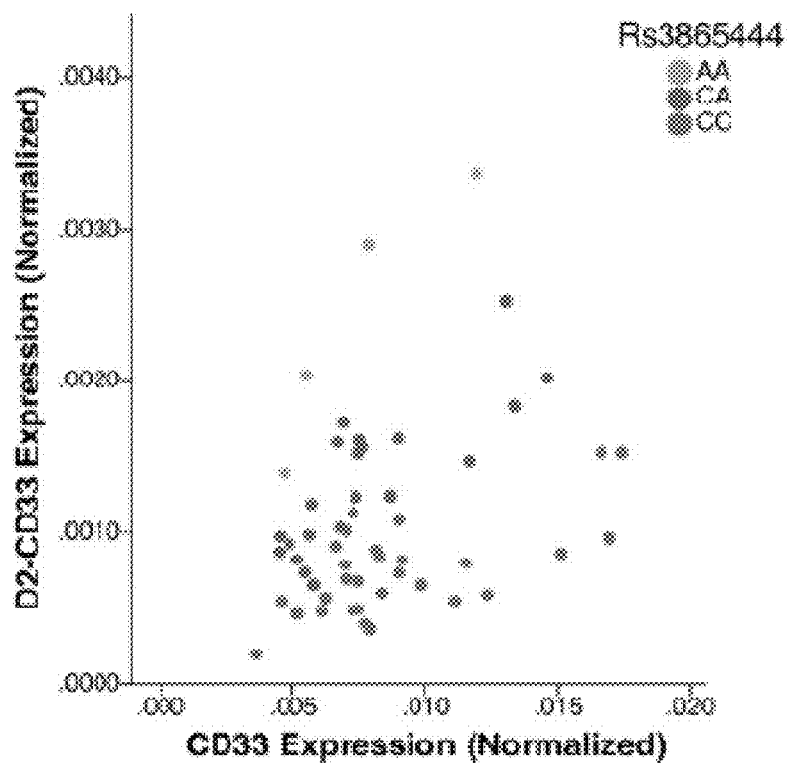
Figure 2D:
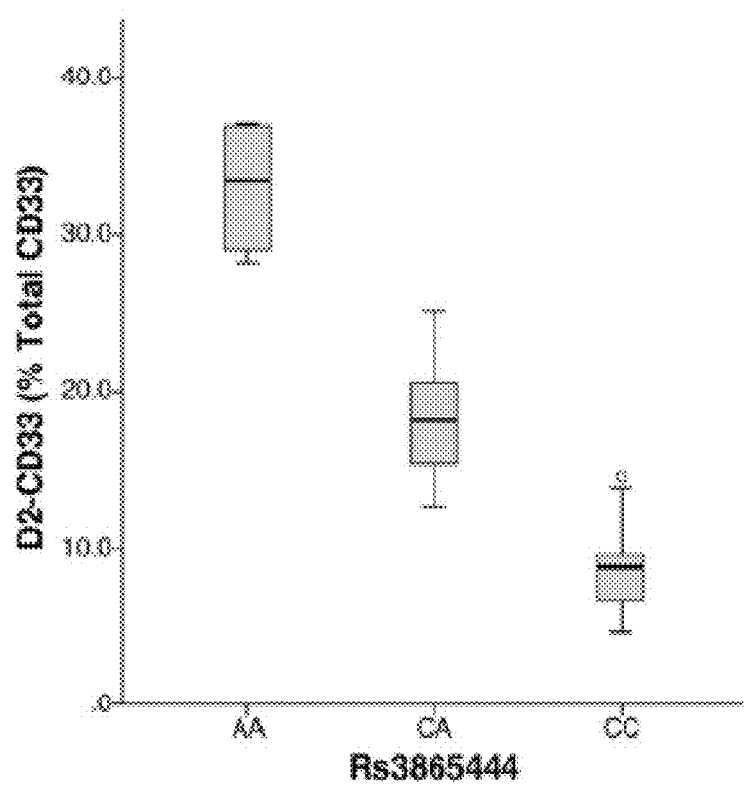

Because D2-CD33 was a common splice variant, D2-CD33 was quantified by performing qPCR with primers corresponding to the exon 1-3 junction and exon 3, as discussed above. D2-CD33 expression was compared with total CD33 expression, and isoform-specific standard curves were analyzed in parallel with samples, which allowed absolute quantitation of each isoform. D2-CD33 expression corresponded with CD33 expression and with rs3865444 genotype (FIG. 2C). When D2-CD33 expression was considered as a percentage of total CD33 expression, the association with rs3865444 genotype was apparent (FIG. 2D). These findings were confirmed by linear regression analyses, which found a significant model (adjusted $r^2=0.75$) with D2-CD33 strongly associated with rs3865444 genotype ($p=1.01\times10^{-13}$, standardized $\beta$ coefficient of 0.81), as well as CD33 expression ($p=2.3\times10^{-10}$, standardized $\beta$ coefficient of 0.58), and decreased with AD status ($p=0.013$, standardized $\beta$ coefficient of $-0.19$). Hence, the proportion of CD33 expressed as D2-CD33 showed a dose-dependent relationship with the rs3865444 allele. Indeed, in this Example the percentage of CD33 expressed as D2-CD33 increased by 10.7±0.8% per copy of the AD-protective rs3865444A allele.

Without being bound by theory or mechanism, since rs3865444 resides in the CD33 promoter, and is therefore unlikely to directly modulate exon 2 splicing, rs3865444 may be coinherited with an SNP near or within exon 2 that modulates exon 2 splicing efficiency. To analyze this finding, CD33 from 400 bp 5% of the transcription start site through exon 4 was sequenced in four rs3865444C/C and three rs3865444A/A individuals, as described above. Four SNPs were observed in these samples: (1) rs3865444; (2) rs2459141 (142 bp upstream of the transcription start site); (3) rs12459419 (the fourth base of exon 2); and (4) rs2455069 (the 168th base of exon 2). Among these variations, only rs12459419 was coinherited with rs3865444 in all seven individuals (i.e., rs3865444AA individuals were also rs12459419TT), whereas rs3865444CC individuals were rs12459419CC. Subsequent rs12459419 genotyping of the samples depicted in FIG. 2 found that rs12459419 major and minor alleles were coinherited with rs3865444 major and minor alleles. Thus, the rs12459419C/T alleles substitute for the rs3865444C/A alleles in FIG. 2.

To evaluate whether rs12459419 is a functional polymorphism and directly modulates exon 2 splicing efficiency, CD33 minigenes for each rs12459419 allele were generated, as discussed above. These minigenes included exon 1 through exon 4, along with intervening introns, and the only difference in minigene sequences was the rs12459419 alleles. This analysis found that D2-CD33 as a percentage of total CD33 increased approximately threefold between cells transfected with rs12459419C (3.4±1.4, mean±SE; n=3) versus rs12459419T minigenes (10.3±2.3, mean±SE; n=3, p=0.034). These findings show that rs12459419 is a functional polymorphism and are consistent with the human brain findings. In silico analysis of RNA binding proteins for the RNA sequence containing rs12459419, GGG(C/U)CUG, predicts that the splicing factor SRSF2 binds when rs12459419C is present but not when rs124594149U is present (scores of 4.1 and 1.4, respectively, threshold score for binding of 2.4). SRSF2 is widely expressed, including immune cells. It thus appears that rs12459419 mediates the rs3865444 association with D2-CD33 expression in brain because rs12459419 is highly coinherited with rs3865444, is the only SNP in exons 1-4 that is coinherited with rs3865444, resides within exon 2, and has a plausible mechanism to modulate splicing.

In summary, CD33 expression is increased in AD and in individuals with the rs3865444C allele that is associated with increased AD risk. Moreover, rs3865444 is associated with CD33 exon 2 splicing efficiency through the exon 2 polymorphism rs12459419, and rs12459419 may also be an appropriate polymorphism for developing AD treatments.

Example 2

This Example extends to the findings of Example 1, and shows that Int1-CD33 is also correlated with rs444. This result steps from the fact that, as shown in Example 1, exon 2 splicing correlates with rs444 genotype.

Using the same methods and materials described in relation to Example 1, an Int1-CD33 specific qPCR assay was generated (FIG. 5). As shown in FIG. 5, Int1-CD33 expression correlated with total CD33 expression (FIG. 5A, adjusted $R^2=0.20$) and with rs444 genotype (FIG. 5B, $p=0.004$). The percentage of CD33 expressed as Int1-CD33 showed a dose-dependent relationship with rs444 allele, increasing 2.3±0.8% per rs444A allele. Since D2-CD33 lacks the ligand binding domain and Int1-CD33 has an early stop codon, the amounts of D2-CD33 and Int1-CD33 were summed as "Non-functional CD33" to estimate the total effect of rs444.

Non-functional CD33 was significantly associated with rs444 ($p=1\times10^{-6}$) in a robust linear model (adjusted $R^2=0.657$) (FIGS. 5C and 5D), with the percentage of CD33 expressed as non-functional-CD33 increasing 13.8±1.9% per copy of AD-protective rs444A allele. It thus appears that there was a significant 13.8% increase per protective rs444A allele in CD33 encoding non-functional CD33 protein. Since rs444A reduces the AD odds ratio to 0.9, more robust CD33 inhibition may reduce AD more robustly. For example, a six times stronger (i.e., about 84%) CD33 inhibition may reduce AD odds ratio to 0.4.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "an antibody" includes a plurality of such antibodies, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

Throughout this document, various references are mentioned. All such references are incorporated herein by reference, including the references set forth in the following list:

REFERENCES

1. Allen M, Zou F, Chai H S, Younkin C S, Crook J, Pankratz V S, Carrasquillo M M, Rowley C N, Nair A A, Middha S, Maharjan S, Nguyen T, Ma L, Malphrus K G, Palusak R, Lincoln S, Bisceglio G, Georgescu C, Schultz D, Rakhshan F, et al. (2012) Novel late-onset Alzheimer disease loci variants associate with brain gene expression. Neurology 79:221-228.
2. Amadori, S. and R. Stasi, Integration of monoclonal antibodies and immunoconjugates into the treatment of acute myeloid leukemia. Curr. Opin. Hematol., 2008. 15(2): p. 95-100.
3. Andrews, R. G., J. W. Singer, and I. D. Bernstein, *Precursors of colony-forming cells in humans can be distinguished from colony-forming cells by expression of the CD33 and CD34 antigens and light scatter properties.* The Journal of experimental medicine, 1989. 169(5): p. 1721-31.
4. Bachstetter, A. D. and L. J. Van Eldik, *The p38 MAP Kinase Family as Regulators of Proinflammatory Cytokine Production in Degenerative Diseases of the CNS.* Aging and disease, 2010. 1(3): p. 199-211.
5. Bachstetter, A. D., B. Xing, L. de Almeida, E. R. Dimayuga, D. M. Watterson, and L. J. Van Eldik, *Microglial p38alpha MAPK is a key regulator of proinflammatory cytokine up-regulation induced by toll-like receptor (TLR) ligands or beta-amyloid (Abeta).* Journal of neuroinflammation, 2011. 8: p. 79.
6. Bradshaw E M, Chibnik L B, Keenan B T, Ottoboni L, Raj T, Tang A, Rosenkrantz L L, Imboywa S, Lee M, Von Korff A; Alzheimer Disease Neuroimaging I, Morris M C, Evans D A, Johnson K, Sperling R A, Schneider J A, Bennett D A, De Jager P L (2013) CD33 Alzheimer's disease locus: altered monocyte function and amyloid biology. Nat Neurosci 16:848-850.

7. Brinkman-Van der Linden E C, Angata T, Reynolds S A, Powell L D, Hedrick S M, Varki A (2003) CD33/Siglec-3 binding specificity, expression pattern, and consequences of gene deletion in mice. Mol Cell Biol 23:4199-4206.
8. Burchett M E, Ling I F, Estus S. FBN1 isoform expression varies in a tissue and development-specific fashion. Biochem Biophys Res Commun. 411: 323-8 (2011).
9. Delrieu, J., P. J. Ousset, C. Caillaud, and B. Vellas, 'Clinical trials in Alzheimer's disease': immunotherapy approaches. J. Neurochem., 2012. 120: p. 186-93.
10. Feldman, E. J., J. Brandwein, R. Stone, M. Kalaycio, J. Moore, J. O'Connor, N. Wedel, G. J. Roboz, C. Miller, R. Chopra, J. C. Jurcic, R. Brown, W. C. Ehmann, P. Schulman, S. R. Frankel, D. De Angelo, and D. Scheinberg, Phase III randomized multicenter study of a humanized anti-CD33 monoclonal antibody, lintuzumab, in combination with chemotherapy, versus chemotherapy alone in patients with refractory or first-relapsed acute myeloid leukemia. J. Clin. Onc., 2005. 23: p. 4110-6.
11. Gonzalez, Y., M. T. Herrera, G. Soldevila, L. Garcia-Garcia, G. Fabian, E. M. Perez-Armendariz, K. Bobadilla, S. Guzman-Beltran, E. Sada, and M. Torres, *High glucose concentrations induce TNF-alpha production through the down-regulation of CD33 in primary human monocytes.* BMC immunology, 2012. 13: p. 19.
12. Grear, K. E., I. F. Ling, J. F. Simpson, J. L. Furman, C. R. Simmons, S. L. Peterson, F. A. Schmitt, W. R. Markesbery, Q. Liu, J. E. Crook, S. G. Younkin, G. Bu, and S. Estus, *Expression of SORL1 and a novel SORLJ splice variant in normal and Alzheimers disease brain.* Mol Neurodegener, 2009. 4: p. 46.
13. Griciuc A, Serrano-Pozo A, Parrado A R, Lesinski A N, Asselin C N, Mullin K, Hooli B, Choi S H, Hyman B T, Tanzi R E (2013) Alzheimer's disease risk gene CD33 inhibits microglial uptake of amyloid beta. Neuron 78:631-643.
14. Griffin, J. D., D. Linch, K. Sabbath, P. Larcom, and S. F. Schlossman, *A monoclonal antibody reactive with normal and leukemic human myeloid progenitor cells.* Leukemia research, 1984. 8(4): p. 521-34.
15. Guerreiro R, Wojtas A, Bras J, Carrasquillo M, Rogaeva E, Majounie E, Cruchaga C, Sassi C, Kauwe J S, Younkin S, Hazrati L, Collinge J, Pocock J, Lashley T, Williams J, Lambert J C, Amouyel P, Goate A, Rademakers R, Morgan K, et al. (2013) TREM2 variants in Alzheimer's disease. N Engl J Med 368:117-127.
16. Guerreiro R J, Beck J, Gibbs J R, Santana I, Rossor M N, Schott J M, Nalls M A, Ribeiro H, Santiago B, Fox N C, Oliveira C, Collinge J, Mead S, Singleton A, Hardy J (2010) Genetic variability in CLU and its association with Alzheimer's disease. PLoS One 5:e9510.
17. Harold D, Abraham R, Hollingworth P, Sims R, Gerrish A, Hamshere M L, Pahwa J S, Moskvina V, Dowzell K, Williams A, Jones N, Thomas C, Stretton A, Morgan A R, Lovestone S, Powell J, Proitsi P, Lupton M K, Brayne C, Rubinsztein D C, et al. (2009) Genome-wide association study identifies variants at CLU and PICALM associated with Alzheimer's disease. Nat Genet 41:1088-1093.
18. Herna'ndez-Caselles T, Martínez-Esparza M, Pe'erez-Oliva A B, Quintanilla-Cecconi A M, García-Alonso A, Alvarez-Lo'pez D M, GarcíaPen-arrubia P (2006) A study of CD33 (SIGLEC-3) antigen expression and function on activated human T and N K cells: two isoforms of CD33 are generated by alternative splicing. J Leukoc Biol 79:46-58.
19. Holler C J, Webb R L, Laux A L, Beckett T L, Niedowicz D M, Ahmed R R, Liu Y, Simmons C R, Dowling A L, Spinelli A, Khurgel M, Estus S, Head E, Hersh L B, Murphy M P. BACE2 expression increases in human neurodegenerative disease. Am. J, Pathol. 180:337-350 (2012).
20. Hollingworth P, Harold D, Sims R, Gerrish A, Lambert J C, Carrasquillo M M, Abraham R, Hamshere M L, Pahwa J S, Moskvina V, Dowzell K, Jones N, Stretton A, Thomas C, Richards A, Ivanov D, Widdowson C, Chapman J, Lovestone S, Powell J, et al. (2011) Common variants at ABCA7, M S4A6A/M S4A4E, EPHAl, CD33 and CD2A P are associated with Alzheimer's disease. Nat Genet 43:429-435.
21. Hsieh, C. L., M. Koike, S. C. Spusta, E. C. Niemi, M. Yenari, M. C. Nakamura, and W. E. Seaman, *A role for TREM2 ligands in the phagocytosis of apoptotic neuronal cells by microglia.* J Neurochem, 2009. 109(4): p. 1144-56.
22. Imbimbo, B. P., S. Ottonello, V. Frisardi, V. Solfrizzi, A. Greco, D. Seripa, A. Pilotto, and F. Panza, Solanezumab for the treatment of mild-to-moderate Alzheimer's disease. *Expert Rev. Clin. Immunol.,* 2012. 8: p. 135-49.
23. Jandus, C., H. U. Simon, and S. von Gunten, *Targeting siglecs—a novel pharmacological strategy for immuno- and glycotherapy.* Biochemical pharmacology, 2011. 82(4): p. 323-32.
24. J Jonsson T, Stefansson H, Steinberg S, Jonsdottir I, Jonsson P V, Snaedal J, Bjornsson S, Huttenlocher J, Levey A I, Lah J J, Rujescu D, Hampel H, Giegling I, Andreassen O A, Engedal K, Ulstein I, Djurovic S, Ibrahim-Verbaas C, Hofman A, Ikram M A, et al. (2013) Variant of TREM2 associated with the risk of Alzheimer's disease. N Engl J Med., 2012, 368:107-116.
25. Jun G, Naj A C, Beecham G W, Wang L S, Buros J, Gallins P J, Buxbaum J D, Ertekin-Taner N, Fallin M D, Friedland R, Inzelberg R, Kramer P, Rogaeva E, St George-Hyslop P, St George-Hyslop P, Cantwell L B, Dombroski B A, Saykin A J, Reiman E M, Bennett D A, et al. (2010) Meta-analysis confirms CR1, CLU, and PICALM as alzheimer disease risk loci and reveals interactions with APOE genotypes. Arch Neurol 67:1473-1484.
26. Lajaunias, F., J. M. Dayer, and C. Chizzolini, Constitutive repressor activity of CD33 on human monocytes requires sialic acid recognition and phosphoinositide 3-kinase-mediated intracellular signaling. *Euro. J. Immunol.,* 2005. 35: p. 243-51.
27. Lambert, J. C., S. Heath, G. Even, D. Campion, K. Sleegers, M. Hiltunen, 0. Combarros, D. Zelenika, et al., Genome-wide association study identifies variants at CLU and CR1 associated with Alzheimer's disease. *Nat. Genet.,* 2009. 41: p. 1094-9.
28. Ling I F, Bhongsatiern J, Simpson J F, Fardo D W, Estus S (2012) Genetics of clusterin isoform expression and Alzheimer's disease risk. PLoS One 7:e33923.
29. Linnartz B, Neumann H (2013) Microglial activatory (immunoreceptor tyrosine-based activation motif)- and inhibitory (immunoreceptor tyrosine-based inhibition motif)-signaling receptors for recognition of the neuronal glycocalyx. Glia 61:37-46.
30. Linnartz B, Wang Y, Neumann H (2010) Microglial immunoreceptor tyrosine-based activation and inhibition motif signaling in neuroinflammation. Int J Alzheimers Dis 2010.pii: 587463.
31. Liu, Z., C. Condello, A. Schain, R. Harb, and J. Grutzendler, *CX3CR1 in microglia regulates brain amyloid deposition through selective protofibrillar amyloid-beta phagocytosis.* The Journal of neuroscience: the official journal of the Society for Neuroscience, 2010. 30(50): p. 17091-101.
32. Morgan, D., D. M. Diamond, P. E. Gottschall, K. E. Ugen, C. Dickey, J. Hardy, K. Duff, P. Jantzen, G. DiCarlo, D. Wilcock, K. Connor, J. Hatcher, C. Hope, M. Gordon, and G. W. Arendash, A beta peptide vaccination prevents memory loss in an animal model of Alzheimer's disease. Nature, 2000. 408: p. 982-5.
33. Morgan K (2011) The three new pathways leading to Alzheimer's disease. Neuropathol Appl Neurobiol 37:353-357.
34. Naj A C, Jun G, Beecham G W, Wang L S, Vardarajan B N, Buros J, Gallins P J, Buxbaum J D, Jarvik G P, Crane P K, Larson E B, Bird T D, Boeve B F, Graff-Radford N R, De Jager P L, Evans D, Schneider J A, Carrasquillo M M, Ertekin-Taner N, Younkin S G, et al. (2011) Common variants at MS4A4/MS4A6E, CD2AP, CD33 and EPHA1 are associated with lateonset Alzheimer's disease. Nat Genet 43:436-441.
35. Nelson P T, Braak H, Markesbery W R (2009) Neuropathology and cognitive impairment in Alzheimer disease: a complex but coherent relationship. J Neuropathol Exp Neurol 68:1-14.
36. Nelson P T, Pious N M, Jicha G A, Wilcock D M, Fardo D W, Estus S, Rebeck G W. APOE-E2 and APOE-E4 Correlate With Increased Amyloid Accumulation in Cerebral Vasculature. J Neuropathol Exp Neurol. 72:708-15 (2013).
37. Neumann H, Daly M J (2013) Variant TREM2 as risk factor for Alzheimer's disease. N Engl J Med 368:182-184.
38. Pe'rez-Oliva A B, Martinez-Esparza M, Vicente-Ferna'ndez J J, Corral-San Miguel R, García-Penarrubia P, Herna'ndez-Caselles T (2011) Epitope mapping, expression and post-translational modifications of two isoforms of CD33 (CD33M and CD33m) on lymphoid and myeloid human cells. Glycobiology 21:757-770.
39. Raza, A., J. G. Jurcic, G. J. Roboz, M. *Maris*, J. J. Stephenson, B. L. Wood, E. J. Feldman, N. Galili, L. E. Grove, J. G. Drachman, and E. L. Sievers, Complete remissions observed in acute myeloid leukemia following prolonged exposure to lintuzumab: a phase 1 trial. *Leuk. & Lymph.*, 2009. 50: p. 1336-44.
40. Scheinberg, D. A., D. Lovett, C. R. Divgi, M. C. Graham, E. Berman, K. Pentlow, N. Feirt, R. D. Finn, B. D. Clarkson, T. S. Gee, and et al., A phase I trial of monoclonal antibody M195 in acute myelogenous leukemia: specific bone marrow targeting and internalization of radionuclide. *J. Clin. Onc.*, 1991. 9: p. 478-90.
41. Sgouros, G., M. C. Graham, C. R. Divgi, S. M. Larson, and D. A. Scheinberg, *Modeling and dosimetry of monoclonal antibody M195 (anti-CD33) in acute myelogenous leukemia*. Journal of nuclear medicine: official publication, Society of Nuclear Medicine, 1993. 34(3): p. 422-30.
42. Simmons C R, Zou F, Younkin S, Estus S. Evaluation of the global association between cholesterol-associated polymorphisms and Alzheimer's disease suggests a role for rs3846662 and HMGCR splicing in disease risk. Mol Neurodegener. 6:62 (2011).
43. Simmons C R, Zou F, Younkin S G, Estus S. Rheumatoid arthritis-associated polymorphisms are not protective against Alzheimer's disease. Mol Neurodegener. 6:33 (2011).
44. Smith, J. D., Moylan, J. S., Hardin, B. J., Chambers, M. A., Estus, S., Telling, G. C., Reid, M. B. Prion protein expression and functional importance in skeletal muscle. Antioxid Redox Signal. 15: 2465-75 (2011).
45. Smith P J, Zhang C, Wang J, Chew S L, Zhang M Q, Krainer A R (2006) An increased specificity score matrix for the prediction of S F2/ASF-specific exonic splicing enhancers. Hum Mol Genet 15:2490-2508.
46. Stasi, R., Gemtuzumab ozogamicin: an anti-CD33 immunoconjugate for the treatment of acute myeloid leukaemia. *Expert Opin. Biol. Ther.*, 2008. 8: p. 527-40.
47. Sutherland, M. K., C. Yu, T. S. Lewis, J. B. Miyamoto, C. A. Morris-Tilden, M. Jonas, J. Sutherland, A. Nesterova, H. P. Gerber, E. L. Sievers, I. S. Grewal, and C. L. Law, Anti-leukemic activity of lintuzumab (SGN-33) in preclinical models of acute myeloid leukemia. *mAbs*, 2009. 1: p. 481-90.
48. Tai L M, Bilousova T, Jungbauer L, Roeske S K, Youmans K L, Yu C, Poon W W, Cornwell L B, Miller C A, Vinters H V, Van Eldik U, Fardo D W, Estus S, Bu G, Gylys K H, Ladu M J. Levels of soluble apolipoprotein E/amyloid-β complex are reduced and oligomeric Aβ increased with APOE4 and Alzheimer disease in a transgenic mouse model and human samples. J Biol Chem. 2013 288:5914-26 (2013).
49. Varki A, Angata T (2006) Siglecs—the major subfamily of I-type lectins. Glycobiology 16:1R-27R. CrossRef Medline
50. Vasquez, J B, Fardo, D W and Estus, S. ABCA7 expression is associated with Alzheimer's disease polymorphism and disease status. Neurosci. Lett. In Press (2013).
51. Visconte V, Makishima H, Maciejewski J P, Tiu R V (2012) Emerging roles of the spliceosomal machinery in myelodysplastic syndromes and other hematological disorders. Leukemia 26:2447-2454.
52. Youmans K L, Tai L M, Nwabuisi-Heath E, Jungbauer L, Kanekiyo T, Gan M, Kim J, Eimer W A, Estus S, Rebeck G W, Weeber E J, Bu G, Yu C, Ladu M J. APOE4-specific changes in Aβ accumulation in a new transgenic model of Alzheimer's Disease. J Biol Chem. 287:41774-86 (2012).
53. Zhu, H., H. M. Tucker, K. E. Grear, J. F. Simpson, A. K. Manning, L. A. Cupples, and S. Estus, *A common polymorphism decreases low-density lipoprotein receptor exon 12 splicing efficiency and associates with increased cholesterol*. Hum Mol Genet, 2007. 16(14): p. 1765-72.
54. Zou F, Gopalraj R K, Lok J, Zhu H, Ling I F, Simpson J F, Tucker H M, Kelly J F, Younkin S G, Dickson D W, Petersen R C, Graff-Radford N R, Bennett D A, Crook J E, Estus S (2008) Sex-dependent association of a common lowdensity lipoprotein receptor polymorphism with RNA splicing efficiency in the brain and Alzheimer's disease. Hum Mol Genet 17:929-935.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of treating Alzheimer's disease in a subject, comprising:
   administering a CD33 antibody to the subject, the subject being identified as having a single nucleotide polymorphism (SNP) selected from rs3865444, rs12459419, and combinations thereof.

2. The method of claim 1, wherein the CD33 antibody includes lintuzumab, P67.6, or combinations thereof.

3. The method of claim 1, further comprising administering to the subject at least one additional component useful for treating Alzheimer's disease.

4. The method of claim 3, wherein the at least one additional component useful for treating Alzheimer's disease is selected from galantamine, rivastigmine, donepezil, tacrine, memantine, vitamin E, and combinations thereof.

5. The method of claim 1, wherein the subject is not being treated for a cancer.

6. The method of claim 1, wherein the subject does not have acute myeloid leukemia (AML) and/or has not been identified as being at risk for developing AML.

* * * * *